United States Patent [19]
Adams et al.

[11] 4,153,807
[45] May 8, 1979

[54] PHENYLALKANOIC ACIDS

[75] Inventors: Stewart S. Adams; Bernard J. Armitage; John S. Nicholson, all of Nottingham, England

[73] Assignee: The Boots Company Limited, Nottingham, England

[21] Appl. No.: 808,007

[22] Filed: Jun. 20, 1977

Related U.S. Application Data

[63] Continuation-in-part of Ser. No. 656,220, Feb. 9, 1976, Pat. No. 4,048,352, which is a continuation-in-part of Ser. No. 367,614, Jun. 6, 1973, Pat. No. 3,769,402.

[30] Foreign Application Priority Data

Jun. 15, 1972 [GB] United Kingdom ............... 28104/72

[51] Int. Cl.$^2$ ............................................. C07C 65/14
[52] U.S. Cl. ...................................... 562/469; 560/59
[58] Field of Search ...................... 260/520 R; 560/59; 562/469

[56] References Cited

U.S. PATENT DOCUMENTS 3,671,580   6/1972   Shen ........................................ 560/59

*Primary Examiner*—Paul J. Killos
*Attorney, Agent, or Firm*—Lawrence Rosen; E. Janet Berry

[57] ABSTRACT

New compounds which are 2-(halogenated-hydroxy-substituted-4-biphenylyl)propionic acids, having, inter alia, anti-inflammatory activity.

6 Claims, No Drawings

PHENYLALKANOIC ACIDS

This application is a continuation-in-part of our application Ser. No. 656,220 filed 9th Feb. 1976, now U.S. Pat. No. 4,048,332 which in turn is a continuation-in-part of our application Ser. No. 367,614 filed 6th June, 1973 now U.S. Pat. No. 3,769,402.

This invention relates to novel substituted propionic acids which have been found to possess valuable biological properties.

According to the invention there is provided a novel 2-(halogenated-2-hydroxy-4-biphenylyl)propionic acid selected from the group consisting of:

2-(4'-chloro-2-hydroxy-4-biphenylyl)propionic acid
2-(2',4'-difluoro-2-hydroxy-4-biphenylyl)propionic acid
2-(2'-chloro-4'-fluoro-2-hydroxy-4-biphenylyl)propionic acid
2-(4'-fluoro-2-hydroxy-4-biphenylyl)propionic acid and
2-(2'-fluoro-2-hydroxy-4-biphenylyl)propionic acid.

The acids may of course be in the form of conventional derivatives such as amine or alkali metal salts and alkyl esters.

The compounds of the invention possess anti-inflammatory activity and are useful for the treatment of inflammatory conditions. They also possess analgesic and antipyretic properties and are useful for the treatment of conditions of pain an pyretic conditions. They activity has been determined in experimental animals using pharmacological tests which are known to be capable of characterising compounds possessing the therapeutic properties of aspirin, namely anti-inflammatory, analgesic and antipyretic activity.

The therapeutic activity of the compounds is assessed in various ways. For example the anti-inflammatory activity is determined in the test described by Adams and Cobb, *Nature* 1958, 181, 733. The activity of the test compounds is compared with that of aspirin against ultra-violet light induced erythema on the depilated skin of guinea pigs.

Another way of determining anti-inflammatory activity is by the rat adjuvant arthritis test in which an arthritis is produced by injecting intradermally into the tail 0.1 ml. of a suspension of killed human tubercle bacilli (6 mg./ml.) in liquid paraffin BP. A polyarthritis develops over the next 3 weeks in untreated controls. The compounds under test (vehicle only for control animals) are given daily by mouth from the day the adjuvant is injected for 21 days. On day 21 the degree of arthritis is assessed on each hind foot. The degree of inhibition produced by a compound is estimated by comparison of the total arthritic scores with those found in the controls.

The analgesic activity of the compounds is determined in the rat using a modification of the technique described by Randall and Selitto, *Arch. int. Pharmacodyn*, 1957, 111, 409. In this technique the analgesic effect of the drugs is compared with aspirin by determining the increase in pain threshold when pressure is applied to the inflammed foot.

The anti-pyretic effect is determined in rats in which the body temperature has been raised by a subcutaneous injection of a yeast suspension. Comparison of the compounds under test is made with graded doses of aspirin.

It will be appreciated that, since the compounds of general formula I possess an asymmetric carbon atom, they are ordinarily present in the form of a racemic mixture. The resolution of such racemates may be carried out by any conventional method and the separated optically active stereoisomers form part of the present invention.

The compounds of the invention may be administered in the conventional manner of aspirin or usual manner for other anti-inflammatory, analgesic, and antipyretic agents, for example orally, topically, rectally or parenterally, preferably orally. The optimum dosage rate varies with the route of administration, but normally lies within the range 0.03–60 mg./kg./day, more usually between 0.70–30 mg./kg./day. The unit dose may vary from 1 mg. to 1000 mg. per subject; for oral administration the dosage rate is preferably 2–2000 mg. per subject per day, optionally in divided doses.

In use, the compounds of the invention are administered in conventional formulations and accordingly the invention also provides therapeutic compositions which comprise, as an active ingredient, a compound of the invention together with a pharmaceutically acceptable carrier. Pharmaceutically acceptable carriers suitable for the production of compositions for oral, topical, rectal or parenteral administration are well known in the art. The compositions of the invention suitably contain 0.1–90% by weight of a compound of the invention.

Compositions for oral administration are the preferred compositions of the invention, and these are the conventional pharmaceutical forms for such administration, such as for example tablets, capsules, lozenges, powders, effervescent granules, syrups and aqueous and oily suspensions. The excipients used in the preparation of these compositions are the excipients of the pharmacist's art. Thus in the preparation of tablets, typical excipients include disintegrating agents, for example maize starch and lubricating agents such as magnesium stearate; in the preparation of capsules, standard gelatin capsules may be used containing the active ingredient alone or admixed with a diluent. The liquid compositions may comprise as excipients water and sucrose to provide syrups, water, dispersing agents and suspending agents, for example sodium carboxymethylcellulose to provide aqueous suspensions, and a non-toxic oil, for example a vegetable oil such as arachis oil and a suspending agent to provide oily suspensions.

Compositions for rectal administration are the conventional pharmaceutical forms for such administration, such as for example suppositories with cocoa butter or polyethylene glycol bases.

Compositions for topical use are the conventional pharmaceutical forms for such application, such as ointments, creams and lotions. Ointments and creams may be water miscible or water-immiscible in character and include emulsions prepared from emulsifying waxes and oils and those prepared from water miscible polyethylene glycols. Lotions may comprise a solution in an aliphatic alcohol with 1-4 carbon atoms which may contain a small proportion of water.

Compositions for parenteral administration are the conventional pharmaceutical forms for such administration, for example sterile suspensions in aqueous or oily media or sterile solutions in propylene glycol.

In some formulations it may be beneficial to use the compounds of the invention in the form of particles of very small size, such as for example, as obtained by fluid energy milling, for example micronizing.

The invention further provides a method of treating inflammatory conditions, conditions of pain and pyretic conditions, individually or in any combination, in warm-blooded animals including man, which comprises administering a compound of the invention, preferably orally.

The products of the present invention may of course be employed in combination with other active anti-inflammatory agents analgesics, and antipyretic agents, or with other drugs, as is already conventional in the art for other existing anti-inflammatory, analgesic and antipyretic materials such as aspirin.

The compounds of the invention have other valuable properties. For example, they possess fibrinolytic and thrombolytic activity and also inhibit platelet aggregation induced by various agents such as adrenaline.

The fibrinolytic activity is assessed by the euglobulin lysistime test described by Van Kaulla in Chemistry of Thrombolysis: Human Fibrinolytic Enzyme, 1963, p79, published by Charles C. Thomas, Springfield, Ill.

The thrombolytic activity is assessed by the hanging clot test described by Van Kaulla, *J. Med. Chem.* 1965, 8, 164.

The effect on platelet aggregation is assessed by the test of Born; *Nature*, 1962, 194, 927.

Drugs possessing such properties are useful in the treatment and/or prophylazis of various thrombotic disorders. When being used in such treatment or prophylaxis they may be formulated and administered in a manner similar to that when being used as anti-inflammatory agents, as described previously.

The compounds of the invention may be prepared by removing any phenolic protecting group X from a compound of the general formula

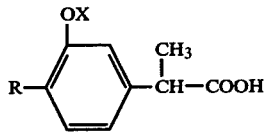

where R is the appropriate halogenated phenyl group.

Phenolic protecting groups X are well known in the art and include, for example, lower alkyl (preferably methyl), benzyl and tetrahydropyranyl. Thus, for example, a lower alkoxy (preferably methoxy) or benzyloxy group may be converted to hydroxy by dealkylation (preferably demethylation) or debenzylation, which may be effected, for example, by heating with HBr in a suitable solvent such as aqueous acetic acid. As another example, benzyloxy may be converted to hydroxy by hydrogenolysis. Such hydrogenolysis may be carried out in a conventional manner, for example by reaction with hydrogen at atmospheric pressure or above in the presence of a suitable catalyst, for example palladium on charcoal or platinum oxide. As a further example, a tetrahydropyranyloxy group may be converted to hydroxy in a conventional manner, for example by reaction with a suitable acid, for example a mineral acid, in a suitable aqueous solvent.

The intermediate compounds of general formula II may be prepared by methods analogous to those described in our British Patent Specification No. 1,091,403 and Belgian Patent Specifications Nos. 764257 and 764258.

The invention is illustrated in the following examples in which "parts" and "percentages" are by weight unless otherwise stated. In the Examples the term "ether" denotes diethyl ether.

EXAMPLE 1

4-fluoroiodobenzene and 4-bromo-3-nitroacetophenone were reacted under Ullmann conditions to give 4-acetyl-4'-fluoro-2-nitrobiphenyl, m.p. 88°–90° C. (from methanol). This compound was reduced with stannous chloride in concentrated hydrochloric acid to give 4-acetyl-2-amino-4'-fluorobiphenyl, m.p. 88°–91° C. (from methanol). The amino group in this compound was converted to methoxy in the following way:

A solution of sodium nitrite (12.0 g.) in water (40 ml.) was added to a stirred solution of 4-acetyl-2-amino-4'-fluorobiphenyl, (36.6 g.) in 5 N sulphuric acid (480 ml.), whilst maintaining the temperature of the reaction mixture at 0°–5° C. The reaction mixture was stirred at 0°–5° C. for a further 1 hour. The resulting cold solution of diazonium salt was poured slowly into stirred refluxing 5 N sulphuric acid (400 ml.). When the addition was complete, refluxing was continued for 0.5 hour. The resulting solution was poured into ice/water, causing the precipitation of a solid which was collected, dried and dissolved in ether. The ethereal solution was extracted with dilute aqueous sodium hydroxide and the extract was acidified to precipitate a product which was extracted into ether. The ethereal extract was washed with water, dried over anhydrous sodium sulphate, and evaporated to give a product which was recrystallized from light petroleum (b.p. 80°–100° C.) to give the novel intermediate 4-acetyl-4'-fluoro-2-hydroxybiphenyl, m.p. 152°–154° C. A mixture of this compound (36.5 g.), dimethyl sulphate (25.2 g.) and potassium carbonate (25 g.) in anhydrous acetone (200 ml.) was refluxed with stirring overnight. Acetone was removed by evaporation, the residue poured into water, and the resulting mixture extracted with ether. The ether extract was washed with dilute sodium hydroxide solution, then with water and dried over anhydrous sodium sulphate. Ether was removed by evaporation and the residue was distilled in vacuo to give a product, b.p. 142°–144° C./0.2 mm. which solidified on cooling. This solid was recrystallized from light petroleum (b.p. 62°–68° C.) to give the novel intermediate 4-acetyl-4'-fluoro-2-methoxybiphenyl, m.p. 75°–77° C.

This was then subjected to a Darzens synthesis using sodium isopropoxide and ethyl chloroacetate and the crude glycidic ester obtained was treated by first sodium hydroxide and then sodium metabisulphite to give 2-(4'-fluoro-2-methoxy-4-biphenylyl)propionaldehyde, b.p. 144°–146° C./0.3 mm. This was treated with hydroxylamine sulphate and sodium acetate to give the oxime which was collected and then treated with aqueous nickel sulphate. The mixture was heated to reflux and aqueous sodium hydroxide added, and reflux continued for 24 hours. The mixture was acidified extracted with ether, the ether extracts extracted with aqueous potassium carbonate, these extracts were acidified and re-extracted with ether, dried and evaporated to give 2-(4'-fluoro-2-methoxy-4-biphenylyl) propionic acid, m.p. 133°–136° C. (from light petroleum, b.p. 100°–120° C.).

A solution of 2-(4'-fluoro-2-methoxy-4-biphenylyl)-propionic acid (10 g.) in a mixture of hydrobromic acid (270 ml. of 48% w/v aqueous acid) and glacial acetic acid (90 ml.) was refluxed for 3.5 hours. The resulting solution was poured onto crushed ice, causing the precipitation of a solid product. This product was collected by filtration, washed with water, dried and recrystallised from chloroform/light petroleum (b.p. 62°–68° C.)

to give 2-(4'-fluoro-2-hydroxy-4-biphenylyl)propionic acid, m.p. 138°–142° C.

EXAMPLE 2

4-Chloroiodobenzene and 4-bromo-3-nitroacetophenone were reacted under Ullman conditions to give the novel intermediate 4-acetyl-4'-chloro-2-nitrobiphenyl, m.p. 103°–105° C. (from methanol). This compound was reduced with stannous chloride and concentrated hydrochloric acid to give 4-acetyl-2-amino-4'-chlorobiphenyl, m.p. 139°–140° C. (from methanol). This compound was converted to the novel intermediate 4-acetyl 4'-chloro-2-hydroxybiphenyl and thence to the novel intermediate 4-acetyl-4'-chloro-2-methoxybiphenyl, b.p. 167°–170° C./0.4 mm., by diazotization and methylation methods analogous to those described in Example 1.

By methods analogous to those described in Example 1, 4-acetyl-4'-chloro-2-methoxybiphenyl was converted to the novel intermediate 2-(4'-chloro-2-methoxy-4-biphenylyl) propionaldehyde, b.p. 174°–175° C./0.7 mm. (solidified on cooling) and thence to the novel intermediate 2-(4'-chloro-2-methoxy-4-biphenylyl)propionic acid, m.p. 127°–128° C. (from light petroleum, b.p. 80°–100° C.)

This was converted to 2-(4'-chloro-2-hydroxy-4-biphenylyl)propionic acid, m.p. 134°–135° C. (from light petroleum, b.p. 80°–100° C.) by reaction with hydrobromic acid in acetic acid in an analogous manner to that described in Example 1.

EXAMPLE 3

By methods analogous to those described in Example 1, 4-acetyl-2-amino-2',4'-difluorobiphenyl was converted to the novel intermediate 4-acetyl-2',4'-difluoro-2-hydroxybiphenyl, m.p. 171°–173° C. (from industrial methylated spirits), and thence to the novel intermediate, 4-acetyl-2',4'-difluoro-2-methoxybiphenyl, m.p. 89°–91° C. (from light petroleum b.p. 62°–68° C.).

This was then converted to 2-(2',4'-difluoro-2-hydroxy-4-biphenylyl)propionic acid, m.p. 138°–140° C. (from chloroform) by reaction with hydrobromic acid in acetic acid.

EXAMPLE 4

By methods analogous to those described in Example 1, 4-acetyl-2-amino-2'-chloro-4'-fluorobiphenyl was converted to the novel intermediate 4-acetyl-2'-chloro-4'-fluoro-2-methoxy biphenyl, m.p. 81.5°–83.5° C. This was converted to crude 2-(2'-chloro-4'-fluoro-2-methoxy-4-biphenylyl)propionaldehyde and thence to the novel intermediate 2-(2'-chloro-4'-fluoro-2-methoxy-4-biphenylyl)propionic acid, m.p. 138°–140° C.

This was then converted to 2-(2'-chloro-4'-fluoro-2-hydroxy-4-biphenylyl)propionic acid, m.p. 155°–157.5° C., by reaction with hydrobromic acid, in acetic acid.

EXAMPLE 5

4-Acetyl-2-amino-2'-fluorobiphenyl was diazotised with sodium nitrite. The diazonium compound was refluxed with sulphuric acid for half an hour and then poured into icewater. The precipitate was extracted in ether, then aqueous sodium hydroxide. This was acidified, to give a brown solid which was washed with water, dried and treated with light petroleum (b.p. 80°–100° C.) in a Soxhlet apparatus. The brown residue which remained was crude 4-acetyl-2'-fluoro-2-hydroxybiphenyl. This was methylated in a similar manner to that described in Example 1 to give almost pure 4-acetyl-2'-fluoro-2-methoxybiphenyl m.p. 84°–85° C. (after recrystallisation from light petroleum (b.p. 62°–68° C.). This was converted to crude 2-(2'-fluoro-2-methoxy-4-biphenylyl)propionaldehyde and thence to the novel intermediate 2(2'-fluoro-2-methoxy-4-biphenylyl)propionic acid m.p. 125°–126° C. which on treatment with hydrobromic acid in acetic acid as described in Example 1, gave 2-(2'-fluoro-2-hydroxy-4-biphenylyl)propionic acid, m.p. 110°–111° C.

EXAMPLE 6

The following mixture was formed into tablets in a conventional manner, each tablet containing 10 mg. of active ingredient.

|  | parts |
|---|---|
| 2-(2'-fluoro-2-hydroxy-4-biphenyl)propionic acid | 5 |
| maize starch | 30 |
| lactose | 158 |
| stearic acid | 1 |
| magnesium stearate | 1 |

Similar tablets are prepared containing as the active ingredient the substituted hydroxy propionic acids of Examples 1 to 5.

We claim:

1. A 2-(halogenated-2-hydroxy-4-biphenylyl)propionic acid selected from the group consisting of:

2-(4'-chloro-2-hydroxy-4-biphenylyl)propionic acid
2-(2',4'-difluoro-2-hydroxy-4-biphenylyl)propionic acid
2-(2'-chloro-4'-fluoro-2-hydroxy-4-biphenylyl)propionic acid
2-(4'-fluoro-2-hydroxy-4-biphenylyl)propionic acid and
2-(2'-fluoro-2-hydroxy-4-biphenylyl)propionic acid.

2. 2-(4'-Chloro-2-hydroxy-4-biphenylyl)propionic acid.

3. 2-(2',4'-Difluoro-2-hydroxy-4-biphenylyl)propionic acid.

4. 2-(2'-Chloro-4'-fluoro-2-hydroxy-4-biphenylyl)-propionic acid.

5. 2-(4'-Fluoro-2-hydroxy-4-biphenylyl)propionic acid.

6. 2-(2'-Fluoro-2-hydroxy-4-biphenyly)propionic acid.

* * * * *